(12) United States Patent
Potter et al.

(10) Patent No.: US 6,214,886 B1
(45) Date of Patent: *Apr. 10, 2001

(54) HYDROXYLATION ACTIVATED PRODRUGS

(75) Inventors: Gerald Andrew Potter, Leicester; Lawrence Hylton Patterson, Anstey; Michael Danny Burke, Houghton on the Hill, all of (GB)

(73) Assignee: DeMontfort University, The Gateway, Leicester (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/115,015

(22) Filed: Jul. 14, 1998

(30) Foreign Application Priority Data

Feb. 6, 1998 (GB) .................................................. 9802552

(51) Int. Cl.$^7$ .................................................. A61K 31/12
(52) U.S. Cl. ............................................................ 514/685
(58) Field of Search ............................ 546/330; 514/357, 514/685

(56) References Cited

U.S. PATENT DOCUMENTS

| | | | |
|---|---|---|---|
| 5,276,058 | 1/1994 | Satoh et al. | 514/646 |
| 5,430,062 | 7/1995 | Cushmann et al. | 514/646 |

FOREIGN PATENT DOCUMENTS 0322738     7/1989    (EP) .

OTHER PUBLICATIONS

Chemical Abstracts, vol. 53, No.9, Abstract 9122, May 1959.*

Klein, Chemical Abstracts, vol. 120, No. 1, Abstract No. 14,657c p. 422, Jan. 1994.*

Tully et al, Journal of Organometallic Chemistry, vol., No. 1, pp. 75–92, 1995.*

Cushman M. et al.: "Syntheisis and Evaluation of Analogues of (Z)–1–(4–Methoxyphenyl)–2–(3,4,5–Trimethoxyphenyl) Ethene As Potential Cytotoxic and Antimitotic Agents"; Journal of Medicinal Chemistry, vol. 35, No. 12, Jun. 12, 1992, pp. 2293–2306, XP000571677; see tables, I, II, IC.

George R. Pettit et al.: "antineoplastic Agents 322. Synthesis of Combretastin A–4 Produgs"; Anti–Cancer Drug Design, vol. 10, 1995, pp. 299–309, XP002102893 see p. 299, line 1–p. 301, line 17 see page 307, line 40–p. 308, line, 12.

Patent Abstracts of Japan; vol. 096, No. 011, Nov. 29, 1996 & JP 08 188546 A (Kyowa Hakko Kogyo Co Ltd), Jul. 23, 1996 see abstract.

Sajjat Hussoin et al.: "Polyhydroxylated Phenylacrylic Acid Derivatives as New Anti–tumor Agents"; Journal of Pharmaceutical Sciences, vol. 80, No. 5, May 1991, pp. 416–418, XP002102894; Washington, US; see p. 417, col. 1, line1—p. 418, col. 2, line 38.

Koji Ohsumi et al.: "Novel Combretastatin Analogues Effective against Murine Solid Tumors: Design and Structure–Activity Relationships"; Journal of Medicinal Chemistry., vol. 41, No. 16, Jul. 30, 1998, pp. 3022–3032, XP002102895; Washington US; see p. 3025, col. 1, line 4—p. 3028, col. 1, line 2; table 1.

Ducki S. et al., "Potent antimitotic and cell growth inhibitory properties of substituted chalcones"; Biorganic & Medicinal Chemistry letters, vol. 8,No. 9, May 1, 1998, p. 1051–1056 XP004137018; see tables 1–3, compounds 2a, 5a; figure 1.

Patent Abstracts of Japan; vol. 010, No. 245 (C–368), Aug. 22, 1986 & JP 61 076433 A (Toyobo Co Ltd), Apr. 18, 1986 see abstract.

Chemical Abstracts, vol. 68, No. 5, Jan. 29, 1968; Columbus OH, US; abstract No. 21141r, G. Pappalardo et al.: "Relation between Structure and Antibacterial Action of Arylthioamides, II. Antibacterial Activity, Ultraviolet and Infrared Spectra, and Acid Hydrolysis of Aryl– and Arylvinylenethioamides" p. 2014; col. 2; XP002102896 see abstract & Farmaco, ed. Sci., vol. 22, No. 10, 1967, pp. 808–820.

\* cited by examiner

Primary Examiner—Zinna Northington Davis
(74) Attorney, Agent, or Firm—BakerBotts, LLP

(57) ABSTRACT

The present invention concerns enzymatic aromatic hydroxylation-activated prodrugs, particularly anti-tumour prodrugs and those which are specifically activated by the hydroxylation activity of the enzyme CYP1B1.

2 Claims, No Drawings

HYDROXYLATION ACTIVATED PRODRUGS

The present invention concerns enzymatic aromatic hydroxylation-activated prodrugs, particularly anti-tumour prodrugs and those which are specifically activated by the hydroxylation activity of the enzyme CYP1B1.

Many conventional cytotoxic drugs are known which can be used for chemotherapeutic purposes. However, they typically suffer from the problem that they are generally cytotoxic and therefore may effect cells other than those which it is wished to destroy. This can be alleviated somewhat by using targetted drug delivery systems, for example direct injection to a site of tumourous tissue, or by e.g. binding the cytotoxic agent to antibody which specifically recognises an antigen displayed by cancerous cells. Alternatively, electromagnetic radiation may be used to cause chemical changes in an agent at a desired site in the body such that it becomes cytotoxic. However, all of these techniques have, to a greater or less extent, certain limitations and disadvantages.

It has been reported (Murray, G. I. et al., Jul. 15, 1997, Cancer Research, 57: 3026–3031) that the enzyme CYP1B1, a member of the cytochrome P450 family of xenobiotic metabolizing enzymes, is expressed at a high frequency in a range of human cancers including cancers of the breast, colon, lung, oesophagur, skin, lymph node, brain and testis, and that is it not detectable in normal tissues. This led to the conclusion (p. 3030, final sentence) that ". . . the expression of CYP1B1 in tumour cells provides a molecular target for the development of new anticancer drugs that could be selectively activated by the presence of CYP1B1 in tumour cells". No specific anticancer drugs are suggested.

The present invention have now succeeded in creating a range of prodrugs which have little or negligible cytotoxic effect when in their normal state, but which are highly cytotoxic (i.e. have a substantially increased cytotoxicity) when hydroxylated by CYP1B1. This provides for a self-targetting drug delivery system in which a non-cytotoxic (or at least negligibly cytotoxic) compound can be administered to a patient, for example in a systemic manner, the compound then being hydroxylated at the site of tumour cells (intratumoural hydroxylation) to form a highly cytotoxic compound which acts to kill the tumour cells. The fact that CYP1B1 is not expressed by normal cells means that the hydroxylation of the compound only occurs at the site of tumour cells and therefore only tumour cells are affected, thus providing a self-targetting drug delivery system.

The prodrugs of the present invention have the distinct advantage of being useful in the treatment of tumours at any site in the body, meaning that even tumours which have undergone metastasis (which are not normally susceptible to site-specific therapies) may be treated, as well of course as primary and secondary tumours.

According to the present invention there is provided a prodrug activated by enzymatic aromatic hydroxylation and having the formula (I):

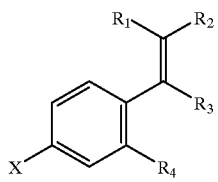

wherein:
X=H, OH or OMe;
$R_1$=H, $C_{1-4}$ lower alkyl, CN or Ar;
$R_2$=H, CN, $CONH_2$, $CSNH_2$, COAr or Ar; and
Ar=phenyl, pyridyl or substituted aryl; and
$R_3$=H or $C_{1-4}$ lower alkyl; and
$R_4$=H, OH or OMe; or;
$R_3$, $R_4$=$(CH_2)_n$, n=2, 3 or 4.

The prodrug may be an anti-tumour prodrug. Examples of tumours include cancers (malignant neoplasms) as well as other neoplasms e.g. "innocent" tumours. The prodrug may be activated by hydroxylation by CYP1B1.

These prodrugs are styrene-derivatives and their specific anti-tumour use is neither suggested nor disclosed by Murray, G. I. et al. (supra), nor is the fact that they are in fact prodrugs having an "activated" hydroxylated form. Where compounds of formula (I) have been previously identified and made, they have not been identified as anti-tumour agents due to their poor (or negligible) cytotoxicity. Thus the intratumoural hydroxylation of the prodrugs of the present invention provides them with a surprising and unexpected efficacy.

The styrene sub-structure of the compounds of formula (I) is essential in providing their efficacy. The Ar group may, for example, be a substituted aryl comprising 4-methoxyphenyl, 4-nitrophenyl, 3,5-dihydroxyphenyl or 3,4,5-trimethoxyphenyl, although other substituted aryls are, of course, also possible.

X may be hydroxy or methoxy.

As specified in formula (I) $R_3$, and $R_4$ may together form an alkyl chain having 2–4 carbon atoms, and thus may form part of a cycloalkyl group having 5, 6 or 7 carbon atoms.

The prodrug may have the formula of any one of formulae (II)–(V):

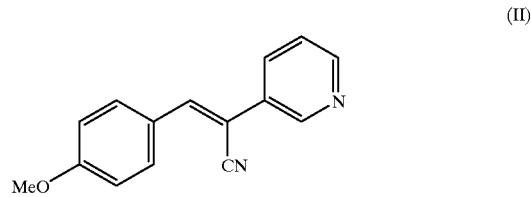

(II)

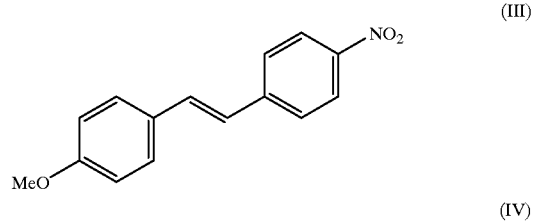

(III)

(IV)

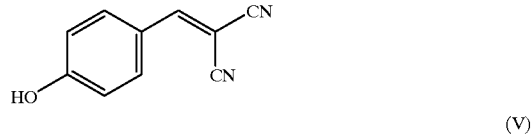

(V)

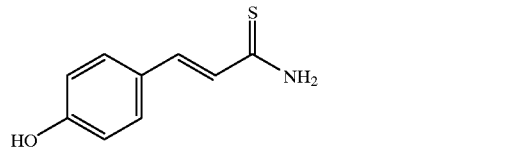

Alternatively, the prodrug may have the formula of either one of formulae (VI) or (VII):

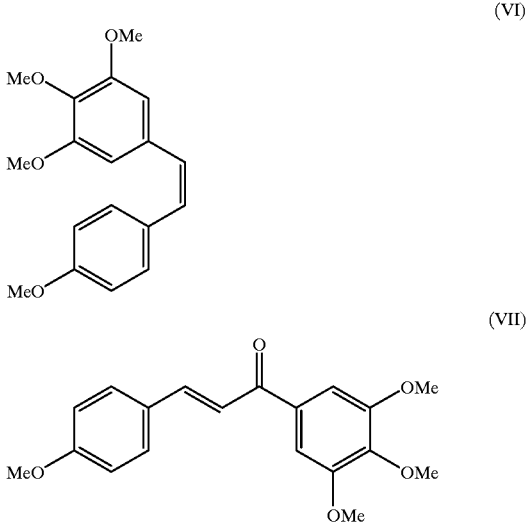

Hydroxylated forms of compounds (II)–(V) are potent tyrosine kinase inhibitors, and hydroxylated forms of compounds (VI) and (VII) are potent antimitotic agents. Previously, tyrosine kinase inhibitors have been of little chemotherapeutic benefit since the tyrosine kinase enzymes are ubiquitous in both normal and tumour cells and are thus not in themselves tumour-specific. However, the targetted production of tyrosine kinase inhibitor in tumour cells means that the inhibitory action will be specific to tumour cells. Furthermore, since the inhibitory activity will only be found in tumour cells, the tyrosine kinase inhibitor itself need not be isoform specific for a particular tyrosine kinase enzyme since any inhibition of tyrosine kinase activity will contribute to tumour inhibition and cell destruction.

Similarly, the antimitotic prodrugs of formulae (VI) and (VII) are particularly useful since present antimitotic agents are of limited use due to the severe side-effects resulting from the poisoning of both normal and tumour cells. The present invention however allows for the specific in situ generation of the antimitotic agent at tumour cells, resulting in their specific targetting.

Methods of synthesis of the prodrugs of the present invention will be readily apparent to one skilled in the art, for example as exemplified below. The compounds of the invention may be prepared in a variety of different ways, for example by aldol condensation (Vogels Textbook of Practical Organic Chemistry, 4th Edition, p. 146), by McMurry coupling (McMurry and Fleming, 1974, J. Am. Chem. Soc., 96:4708–4709), or by the Wittig reaction (1973, Org. Synth. Coll., 5:751).

Also provided according to the present invention is a prodrug according to the present invention for use in a method of treatment or diagnosis of the human or animal body, particularly the treatment or diagnosis of tumours.

Also provided according to the present invention is the use of a prodrug according to the present invention in the manufacture of a medicament for the treatment of tumours.

Also provided according to the present invention is a method of manufacture of a medicament, comprising the use of a prodrug according to the present invention. The medicament may be for the treatment of a tumour.

Also provided according to the present invention is a method of treatment or diagnosis of a tumour in a patient, comprising administering to the patient a prodrug according to the present invention.

Methods of manufacture of medicaments are well known. For example a medicament may additionally comprise a pharmaceutically acceptable carrier, diluent or excipient (Reminton's Pharmaceutical Sciences and US Pharmacopoeia, 1984, Mack Publishing Company, Easton, Pa. USA).

The exact dose (i.e. a pharmaceutically acceptable dose) of prodrug to be administered to a patient may be readily determined by one skilled in the art, for example by the use of simple dose-response experiments.

Since the prodrugs of the present invention are specific to tumour cells, they may not only be used to treat tumours, but may also be used to determine whether or not a patient (or a sample taken from a patient) has tumour cells. For example, cell numbers in a sample may be assayed, as may the presence and quantity of the hydroxylated prodrug, thus providing for the diagnosis of the presence of tumour cells.

Also provided according to the present invention is the hydroxylated form of a prodrug according to the present invention.

The invention will be further apparent from the following description, which shows, by way of example only, forms of prodrugs.

Prodrugs according to the present invention were synthesised as described below and the products of their hydroxylated metabolites assayed for the presence of the desired hydroxylation products.

Microsomal Preparation of Resected Human Tumour Tissue

A microsomal preparation of human tumour tissue expressing the CYP1B1 enzyme was prepared essentially as described by the method of Barrie et al., (1989, J. Steroid Biochem., 6: 1191–1195).

Metabolism Studies

Experiment were carried out at 37° C., under yellow light. An array of 1.5 ml centrifuge tubes were set up in a water bath shaker under aerobic conditions. To each tube was then added 500 µl of pH 7.6 buffer (0.1 M $NaK_2PO_4$), followed by NADPH (5 µl of a 25 mM stock solution). The microsomal preparation (80 µl) was then added and the tubes preincubated for 5 minutes at 37° C. The prodrug substrate was then added (10 µl of a 5 mM stock solution) and incubated for 1 hour at 37° C. After 1 hour the tubes were transferred to an ice/water cooling bath (0° C.). The tubes were then centrifuged at 15,000 rpm for 30 minutes. A sample of the supernatant (100 µl) was then taken and analysed by HPLC.

HPLC conditions: Spherisorb C18 (25 cm×4.6 mm id), used without guard column. Flow rate 1 ml/min. Eluent 75% 0.1 M $KH_2PO_4$ and 25% acetonitrile.

The prodrugs were assayed as described above and were found to undergo aromatic hydroxylation. The hydroxylated metabolite was detected by HPLC, and confirmed by synthesis of the authentic hydroxylated metabolite.

Compound IIa (below), (Z)-1-Cyano-1-(3-pyridyl)-2-(4-methoxyphenyl)ethene, was converted to the hydroxylated metabolite (Z)-1-Cyano-1-(3-pyridyl)-2-(3-hydroxy-4-methoxyphenyl)ethene.

Compound IIIc, (E)-(3,4',5)-trihydroxystilbene was converted to the hydroxylated metabolite (E)-(3,3',4,5')-tetrahydroxystilbene.

Compound VII (E)-1-(4-Methoxyphenyl)-3-(3,4,5-trimethoxyphenyl)prop-1-en-3-one was converted to the hydroxylated metabolite (E)-1-(3-Hydroxy-4-methoxyphenyl)-3-(3,4,5-trimethoxyphenyl)prop-1-en-3-one.

Methods of Synthesis

Compound IIa-(Z)-1-Cyano-1-(3-pyridyl)-2-(4-methoxyphenyl)ethene

To a stirred mixture of 4-methoxybenzaldehyde (2 g, 14.69 mmol) and 3-pyridylacetonitrile (1.58 ml, 14.84 mmol) in methanol (30 ml) was added 50% w/v sodium hydroxide (1 ml). The reaction was stirred for 3 hours. The reaction mixture was quenched with water (20 ml), acidified with 2N HCl, then rebasified with dilute NaOH (aq), and the reaction product was extracted successively into dichloromethane (3×20 ml). The organic solutions were dried over anhydrous $MgSO_4$ and the solvent removed. Purification by column chromatography ($SiO_2$, Hexane/Ethylacetate 8:2; 1:1) gave 2.01 g (58% yield) of compound 1 as a straw coloured solid: 1H-NMR (CDCl3): (8.80 (d, 1H), 8.50 (m, 1H), 7.80 (m, 3H), 7.45 (s, 1H), 7.25 (m, 1H), 6.90 (m, 2H), 3.80 (s, 3H). 13C NMR (CDCl3): (161.9, 157.6, 157.5, 149.5, 146.9, 143.3, 133.1, 131.4, 130.9, 126, 123.5, 117.7, 114.5, 105.2, 55.4. Mass Spectrum m/e (M+1) 237.

Hydroxylated Metabolite of Compound IIa

-(Z)-1-Cyano-1-(3-pyridyl)-2-(3-hydroxy-4-methoxyphenyl)ethene

A mixture of 4-methoxy-3-hydroxylbenzaldehyde (0.5 g, 3.3 mmoles), 3-pyridylacetonitrile (0.35 ml, 3.3 mmoles) and 50% w/v of aqueous NaOH (3 ml) in methanol (10 ml) was stirred at room temperature for 30 minutes. A yellow solid precipitated was filtered, washed with cooled methanol (1 ml), cooled $CH_2Cl_2$ (5 ml) and dried under vacuum over $P_2O_5$ to yield 0.5 g (60%) of compound 3 was yellow solid: 1H-NMR (CD3OD): (8.8 (m, 1H), 8.5 (m, 1H), 7.7 (s, 1H), 7.5 (m, 1H), 7.3 (d, 1H), 7.2 (d, 1H), 6.8 (d, 1H); Mass Spectrum m/e (M+1) 253.

Compound IIb—(Z)-1-Cyano-1-(3-pyridyl)-2-(4-hydroxyphenyl)ethene

A mixture of 4-hydroxylbenzaldehyde (0.5 g, 4.1 mmoles), 3-pyridylacetonitrile (0.54 ml, 4.1 mmoles) and 50% w/v of aqueous NaOH (3.3 ml) in methanol (10 ml) was stirred at room temperature for 30 minutes. A yellow precipitate formed was filtered, washed with cooled methanol (1 ml), cooled $CH_2Cl_2$ (10 ml) and dried under vacuum over $P_2O_5$ to yield 0.6 g (66%) of compound 2: 1H-NMR (CD3OD): (8.8 (d, 1H), 8.4 (m, 1H), 8.05 (m, 1H), 7.8 (m, 2H), 7.6 (s, 1H), 7.4 (m, 1H), 6.6(m, 2H). 13C-NMR (DMSO): (177.52, 175.57, 146.59, 145.06, 144.78, 133.15, 132.73, 130.97, 123.8, 120.8, 120.3, 114.3, 88.5; Mass Spectrum m/e (M+1) 223.

Compound IIIb (via McMurry Coupling)—(E)-(4,4')-Dimethoxystilbene $LiAlH_4$ (0.5 g, 13.18 mmoles) was added to a stirred slurry of $TiCl_3$ (3.13 g, 26.35 mmol) under $N_2$ in dry THF (20 ml). Instantaneous reaction occurred accompanied by the evolution of heat and gas and by a rapid change of colour to deep black. A THF solution of 4-methoxybenzaldehyde (1.79, 13.18 mmoles) was added. The mixture was refluxed for 4 hours. The reaction was quenched with cooled $H_2O$ (2 ml), extracted into ethylacetate (5×20 ml) and purified by column chromatography. Mass Spectrum m/e (M+1) 241.

Compound IIIb (via Wittig Reaction)—(E)-(4,4')-Dimethoxystilbene 4-methoxybenzyltriphenylphosphonium chloride (0.5 g, 1.19 mmoles) was added over a 5 minute period to DMF (20 ml). The solution was stirred for 4 hours at room temperature. 4-methoxybenzaldehyde (0.16 g, 1.19 mmol) was added and the mixture refluxed for 24 hours, solvent concentrated. The crude compound was purified by column chromatography.

Compound VII—(E)-1-(4-Methoxyphenyl)-3-(3,4,5-trimethoxyphenyl)prop-1-en-3-one

To a stirred solution of 4-methoxylbenzaldehyde (1.0 g, 7.3 mmol) and 3,4,5-trimethoxyacetophenone (1.54 g, 7.3 mmol) in methanol (30 ml) was added a 50% w/v solution of aqueous NaOH (1 ml). The mixture was stirred for 24 hours at room temperature, acidified with 2N HCl and extracted with chloroform (3×30 ml). The combined organic phase was dried over anhydrous $MgSO_4$, filtered, and the solvent concentrated under vacou. The product was finally purified by column chromatography. Mass Spectrum m/e (M+1) 329.

Hydroxylated Metabolite of Compound VII (E)-1-(3-Hydroxy-4-methoxyphenyl)-3-(3,4,5-trimethoxyphenyl)prop-1-en-3-one To a stirred solution of 3-hydroxy-4-methoxybenzaldehyde (1.1 g, 7.3 mmol) and 3,4,5-trimethoxyacetophenone (1.54 g, 7.3 mmol) in methanol (30 ml) was added a 50% w/v solution of aqueous NaOH (1 ml). The mixture was stirred for 24 hours at room temperature, acidified with 2N HCl and extracted with chloroform (3×30 ml). The combined organic phase was dried over anhydrous $MgSO_4$, filtered, the solvent concentrated under vacou. The product was purified by crystallisation from methanol. 1H-NMR (CDCl3): 7.8 (d, 1H), 7.4 (d, 1H), 7.2–7.3 (m, 3H), 7.1 (dd, 1H), 6.9 (d, 1H), 5.8 (s, 1H) 4.0 (s, 9H) 3.9 (s, 3H); Mass Spectrum m/e (M+1) 329.

What is claimed is:

1. A method of inhibiting growth of tumor cells containing an aromatic hydroxylase enzyme comprising contacting the tumor cells with a prodrug having the formula

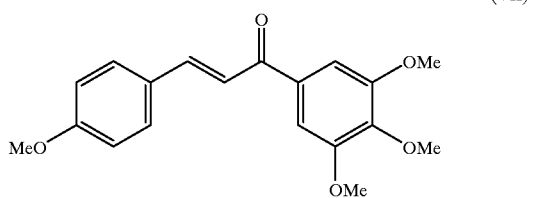

(VII)

2. The method of claim 1 wherein the aromatic hydroxylase enzyme is CYP1B1.

* * * * *